(12) United States Patent
Varga et al.

(10) Patent No.: US 9,446,211 B2
(45) Date of Patent: Sep. 20, 2016

(54) RESUSCITATION DEVICE WITH ONBOARD PROCESSOR

(71) Applicant: CareFusion 2200, Inc., San Diego, CA (US)

(72) Inventors: Christopher Varga, Laguna Hills, CA (US); Dennis White, Yorba Linda, CA (US); Michael McMahon, Anaheim Hills, CA (US)

(73) Assignee: CareFusion 2200, Inc., San Diego, CA (US)

( * ) Notice: Subject to any disclaimer, the term of this patent is extended or adjusted under 35 U.S.C. 154(b) by 679 days.

(21) Appl. No.: 13/829,281

(22) Filed: Mar. 14, 2013

(65) Prior Publication Data

US 2014/0275820 A1    Sep. 18, 2014

(51) Int. Cl.
*A61M 16/00* (2006.01)
*A61B 5/01* (2006.01)
*A61B 5/08* (2006.01)
*A61B 5/00* (2006.01)
*A61B 5/087* (2006.01)
*A61M 16/04* (2006.01)
(Continued)

(52) U.S. Cl.
CPC ............ *A61M 16/0078* (2013.01); *A61B 5/01* (2013.01); *A61B 5/082* (2013.01); *A61B 5/0876* (2013.01); *A61B 5/4836* (2013.01); *A61M 16/0051* (2013.01); *A61M 16/0084* (2014.02); *A61B 5/0002* (2013.01); *A61B 5/74* (2013.01); *A61M 16/04* (2013.01); *A61M 16/06* (2013.01); *A61M 16/208* (2013.01); *A61M 2016/0021* (2013.01); *A61M 2016/0027* (2013.01); *A61M 2016/0033* (2013.01); *A61M 2202/0208* (2013.01); *A61M 2205/3303* (2013.01); *A61M 2205/3324* (2013.01); *A61M 2205/3368* (2013.01); *A61M 2205/3592* (2013.01); *A61M 2205/50* (2013.01); *A61M 2205/502* (2013.01); *A61M 2205/52* (2013.01); *A61M 2205/581* (2013.01); *A61M 2205/583* (2013.01); *A61M 2205/8212* (2013.01); *A61M 2230/42* (2013.01); *A61M 2230/432* (2013.01)

(58) Field of Classification Search
None
See application file for complete search history.

(56) References Cited

U.S. PATENT DOCUMENTS

2002/0117173 A1   8/2002 Lynn et al.
2002/0185127 A1* 12/2002 Melker et al. ........... 128/202.22
(Continued)

OTHER PUBLICATIONS

International Search Report and Written Opinion in PCT Application No. PCT/US2014/019634 dated Sep. 4, 2014, 17 pages.
(Continued)

*Primary Examiner* — Jacqueline Cheng
*Assistant Examiner* — Jairo Portillo
(74) *Attorney, Agent, or Firm* — McDermott Will & Emery LLP (57) ABSTRACT

A resuscitator has a patient airway interface device, a bag, a flow passage coupled between the bag and patient airway interface device, and a sensor assembly. The patient airway interface device may be a mask or an endotracheal tube. The sensor assembly has a display, at least one sensor coupled to the flow passage and configured to provide a measurement of at least one parameter, and a processor coupled to the display and the at least one sensor. The processor is configured to receive the measurement from the sensor and provide information on the display based on the received measurement. The information may include a current breath rate, a pressure-vs-time curve, and guidance to the user to assist in achieving a target breath rate.

29 Claims, 6 Drawing Sheets

(51) Int. Cl.
*A61M 16/06* (2006.01)
*A61M 16/20* (2006.01)

(56) References Cited

U.S. PATENT DOCUMENTS

| | | | |
|---|---|---|---|
| 2004/0015091 A1* | 1/2004 | Greenwald et al. | 600/513 |
| 2007/0068810 A1* | 3/2007 | Tsukashima et al. | 204/433 |
| 2007/0261698 A1 | 11/2007 | Palatnik | |
| 2008/0053445 A1 | 3/2008 | Kroupa et al. | |
| 2008/0214948 A1 | 9/2008 | Myklebust et al. | |
| 2009/0064794 A1* | 3/2009 | Bonassa | 73/861.61 |
| 2011/0284004 A1* | 11/2011 | Silver et al. | 128/205.13 |
| 2012/0302910 A1 | 11/2012 | Freeman et al. | |

OTHER PUBLICATIONS

Ventlab Adult Resuscitator VN1000 Series, http://www.ventlab.com/natsyn/adult_printable_insert.pdf, accessed Feb. 12, 2013.

Kharitonov, Sergei A., et al., "Exhaled Markers of Pulmonary Disease," Imperial College, London, United Kingdom, American Journal of Respiratory and Critical Care Medicine, vol. 163, 2001, pp. 1693-1722.

Jackson, Abigail S., et al., "Comparison of Biomarkers in Exhaled Breath Condensate and Bronchoalveolar Lavage," Department of Thoracic Medicine, St. Vincent's Hospital, Australia, American Journal of Respiratory and Critical Care Medicine, vol. 175, 2007, pp. 222-227.

* cited by examiner

RESUSCITATION DEVICE WITH ONBOARD PROCESSOR

CROSS-REFERENCES TO RELATED APPLICATIONS

Not applicable.

BACKGROUND

1. Field

The present disclosure generally relates to manual resuscitation devices and, in particular, a resuscitator that incorporates electronic sensing and processing.

2. Description of the Related Art

A resuscitator, sometimes referred to as a bag valve mask (BVM) or by the proprietary name "Ambu bag," is a hand-held device used to provide positive pressure ventilation to a patient who is not breathing or who is breathing inadequately. The resuscitator is a normal part of a "crash cart" used within a hospital or a resuscitation kit provided to ambulance crew. A resuscitator may also be used in an operating room to ventilate an anaesthetized patient prior to attachment of a mechanical ventilator. A resuscitator may be self-filling with air or provided with a source of breathing gas, such as oxygen, to increase the oxygenation of the patient.

Figure 1:
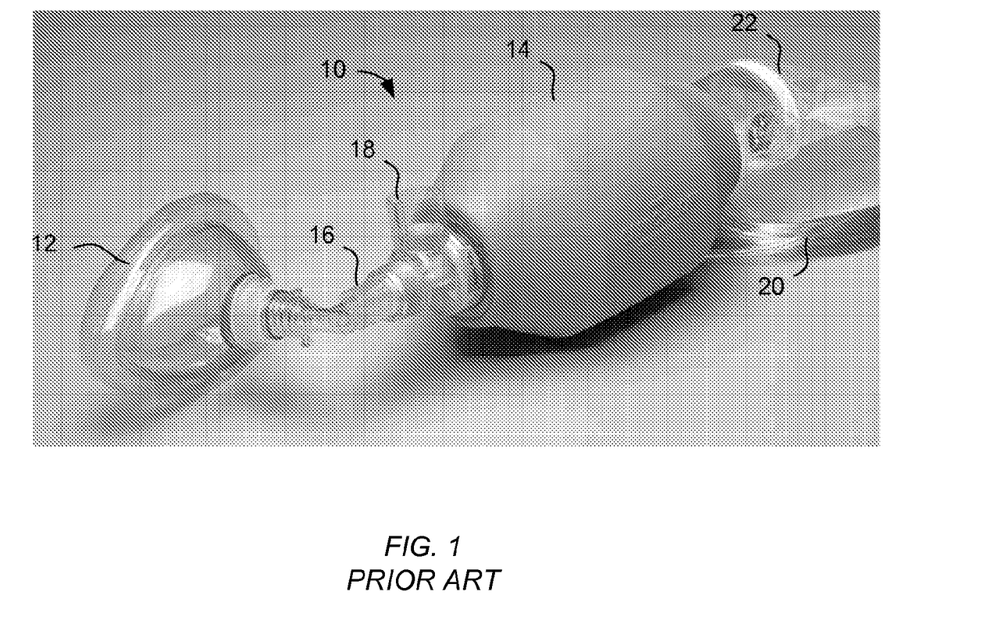
FIG. 1 depicts a conventional resuscitator.

FIG. 1 depicts a conventional resuscitator 10 that is connected to a line 20 that provides oxygen or other breathing gas. A bag 14 is connected to a mask 12 by a flow channel 16 that also has a valve assembly 18 that prevents backflow into the bag 14 and diverts exhaled gas to the atmosphere. An accumulator bag 22 is connected at the junction of the bag 14 and line 20 to accumulate a reservoir of oxygen such that the self-expansion of the bag 14 is not limited by the flow rate of line 20.

When using a resuscitator, there is a risk of over-inflating the lungs. This can lead to pressure damage to the lungs themselves and can also cause air to enter the stomach, causing gastric distension which can make it more difficult to inflate the lungs. Over-inflation may also cause the patient to vomit, which can cause additional airway problems beyond the original breathing difficulty.

Figure 2:
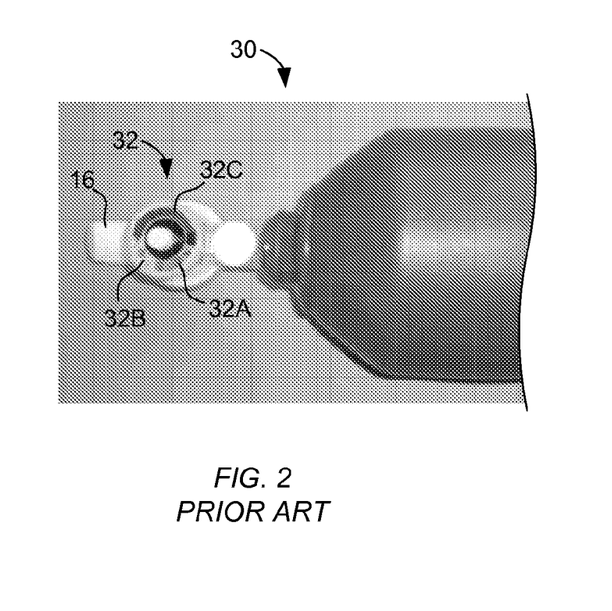
FIG. 2 depicts a conventional resuscitator having a mechanical pressure gauge.

FIG. 2 depicts another conventional resuscitator 30 having a mechanical pressure gauge 32 connected to the flow channel 16. The gauge 32 is marked with a green zone to indicate the desirable range of inflation pressure as well as yellow and red zones to indicate zones of excess inflation pressures. These types of mechanical gauges have limited resolution and reading such a gauge can be a challenge for caregivers as the gauge provides only an instantaneous reading and the caregiver cannot pay constant attention to the gauge as they may be performing other actions, for example striving to maintain a proper seal of the mask to the patient's face and monitoring other symptoms and aspects of the patient's condition.

SUMMARY

The resuscitator disclosed herein provides automatic monitoring of various aspects of the operation of the resuscitator as well as the patient's breathing and exhaled breath. The information gathered by the resuscitator can be provided in real-time to the caregiver to aid in their resuscitation efforts or stored for later review and analysis.

In certain embodiments, a resuscitator is disclosed that includes a patient airway interface device, a bag, a flow passage coupled between the bag and patient airway interface device, and a sensor assembly. The sensor assembly may have a display, at least one sensor coupled to the flow passage and configured to provide a measurement of at least one parameter, and a processor coupled to the display and the at least one sensor. The processor may be configured to receive the measurement from the at least one sensor and provide information on the display based on the received measurement.

In certain embodiments, a resuscitator is disclosed that includes a patient airway interface device, a bag, a flow passage coupled between the bag and patient airway interface device, and a sensor assembly having an indicator, at least one sensor coupled to the flow passage and configured to provide a measurement of at least one parameter, and a processor coupled to the indicator and the at least one sensor. The processor is configured to receive the measurement from the at least one sensor and actuate the indicator based on the received measurement.

In certain embodiments, a method is disclosed that includes the steps of measuring at least one of a flow rate, a pressure, a temperature, a pH, and a chemical marker in the exhaled breath of a patient; and actuating an indicator so as to provide information related to at least one of a breath rate, a tidal volume, a pressure-vs-time curve, a presence of a chemical in the patient's breath, or a condition of the patient.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The resuscitator disclosed herein provides automatic monitoring of various aspects of the operation of the resuscitator as well as the patient's breathing and exhaled breath. The information gathered by the resuscitator can be provided in real-time to the caregiver to aid in their resuscitation efforts or stored for later review and analysis.

In general, the disclosed resuscitator may include sensors that continuously or intermittently measure the pressure within the patient airway interface device and, during an exhalation by the patient, may measure one or more of chemical markers or particular chemicals, temperature, or pH. The resuscitator may also provide guidance to the caregiver such as a metronome of the optimal rate of inhalations, visual or audible alarms, and verbal communication.

This disclosure describes embodiments that include a mask intended to be placed over a patient's nose and/or mouth so as to form a sealed connection to the patient's airway. It should be understood that other types of patient airway interfaces may be used in place of the mask, for example an endotracheal tube, without departing from the scope of this disclosure. In general, the term "mask" includes all types of patient airway interface devices.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

FIG. 1 depicts a conventional resuscitator 10. A flexible mask 12 is configured to be placed over a patient's mouth and nose. The bag 14 is connected to the mask 12 by a flow channel 16. A valve assembly 18 is attached to the flow channel 16 and includes a valve (not visible in FIG. 1) that prevents an exhaled breath from entering the bag 14 and diverts the exhaled breath out a port to the ambient atmosphere. This resuscitator 10 may be attached to a line 20 that provides oxygen, or other breathing gas, with an accumulator bag 22 connected at the junction of the bag 14 and line 20 to accumulate a reservoir of oxygen such that the self-expansion of the bag 14 is not limited by the flow rate of line 20.

FIG. 2 depicts another conventional resuscitator 30 having a mechanical pressure gauge 32 connected to the flow channel 16. The gauge 32 is marked with a green zone 32A to indicate the desirable range of inflation pressure as well as a yellow zone 32B and a red zone 32C to indicate zones of excess inflation pressures. As the gauge 32 provides only an instantaneous reading, there is no information regarding the history of the pressure being provided during the inhalation intervals or an average pressure. In addition, the mechanical inertia of the gauge 32 may delay or dampen the displayed value compared to the true instantaneous pressure in the flow channel 16.

Figure 3:
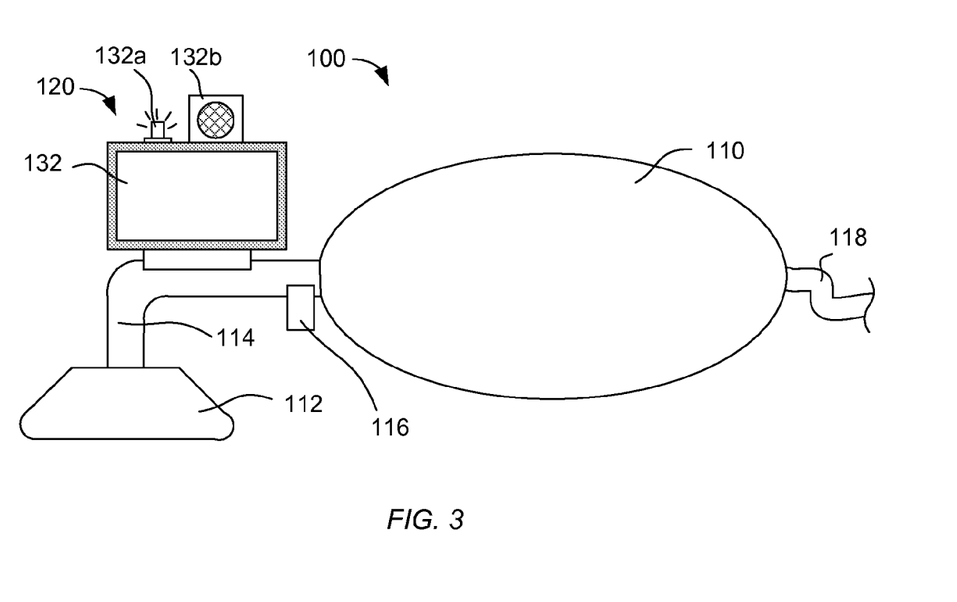
FIG. 3 is a schematic representation of an exemplary resuscitator according to certain aspects of the present disclosure.

FIG. 3 is a schematic representation of an exemplary resuscitator 100 according to certain aspects of the present disclosure. The resuscitator 100 includes a bag 110 connected to a mask 112 through a flow passage 114. In certain embodiments, the bag 110 is manually squeezed to force air or other breathing gas into the patient's lungs, after which the bag 110 self-expands to draw in new air or gas. A valve assembly 116, containing a shutter valve (not visible in FIG. 3) or equivalent, is attached to the flow passage 114 to divert exhaled gas to the atmosphere. A sensor module 120 that includes a display 132 is coupled, in this example, to the flow passage 114 between the mask 112 and the valve assembly 116. In certain embodiments, the sensor assembly 120 is operatively coupled to the valve assembly 116. The sensor assembly 120 is discussed in greater detail with respect to FIG. 4. In certain embodiments, the mask 112 may be replaced by other types of breathing interface devices, for example an endotracheal tube or laryngeal mask airway (not shown in FIG. 3). In certain embodiments, the bag 110 draws in a breathing gas, for example oxygen, through an attached line 118. In certain embodiments, a reservoir (not shown in FIG. 3) may be attached proximate to the junction of the line 118 and bag 110 to provide a large volume of the breathing gas such that the self-expansion of the bag 110 is not limited by the flow rate of line 118.

Figure 4:
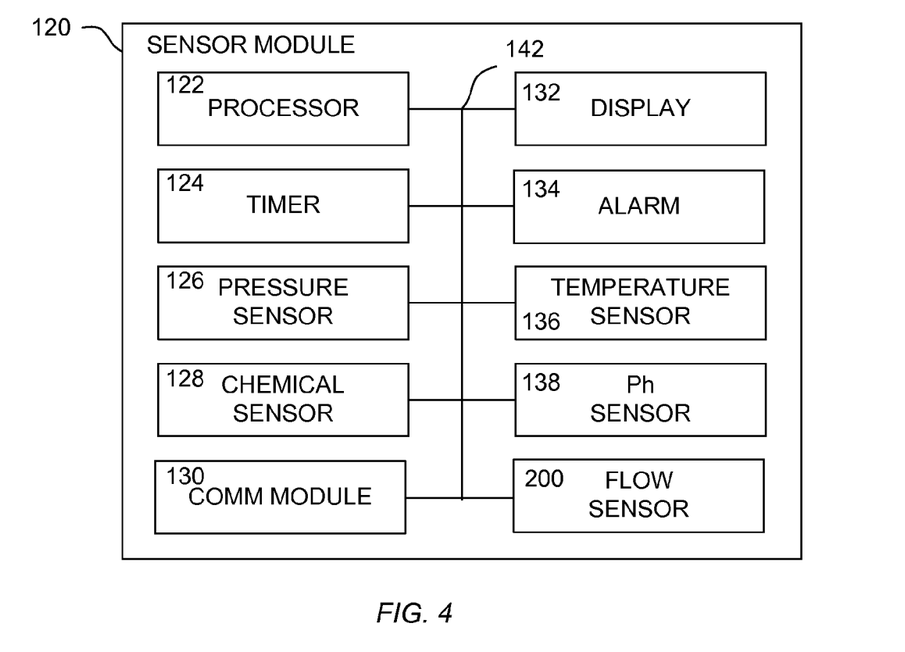
FIG. 4 is a block diagram of the example sensor module that is part of the resuscitator of FIG. 3 according to certain aspects of the present disclosure.

FIG. 4 is a block diagram of the example sensor module 120 that is part of the resuscitator 100 of FIG. 3 according to certain aspects of the present disclosure. The sensor module 120 may include one or more of a processor 122, a timer 124, a pressure sensor 126, a chemical sensor 128, a communication (comm) module 130, a display 132, an alarm 134, a temperature sensor 136, and a pH sensor 138 that are interconnected by a network 142. Other elements common to electronic equipment, for example batteries or power supplies, touch screen interfaces, buttons, switches, and connectors, that are known to those of skill in the art are omitted so as not to obscure the disclosed features. The processor 122 is discussed in greater detail with respect to FIG. 5. The flow sensor 200 is discussed in greater detail with respect to FIG. 6.

The pressure sensor 126 may be any device or mechanism configured to measure a gas pressure as are known to those of skill in the art. The pressure sensor 126, as well as one or more of the other sensors 128, 136, 138, and 200, may include resistive, capacitive, piezoelectric, or solid state electronic devices with or without embedded signal-conditioning circuitry. In certain embodiments, the pressure sensor 126, or other sensor, may be configured to detect an initial manual compression of the resuscitator bag 110 and trigger certain functions, for example turning on the display 132 and powering up other elements of the sensor module 120. In certain embodiments, the pressure sensor 126 or other sensor may be configured to detect inactivity over a determined period of time and trigger other functions, for example turning off the display 132 and placing the CPU in a low-power state to conserve power.

The chemical sensor 128 may include one or more sensors that may be configured to detect in the patient's exhaled breath the presence or amount of certain chemical markers associated with certain physical attributes. In certain embodiments, the chemical sensor 128 may detect or measure markers associated with a level of alcohol or a drug in the patient's blood. In certain embodiments, the chemical sensor 128 may detect or measure a peroxide level in the patient's breath that may be associated with asthma. In certain embodiments, the chemical sensor 128 may measure one or more partial pressures of certain gases, for example carbon dioxide, in the patient's exhaled breath.

The comm module 130 may include a wireless communication system, for example using Bluetooth® (IEEE 802.15.1) or Wi-Fi (IEEE 802.11) elements and protocols, that allows the sensor module 120 to communicate with external equipment. In certain embodiments, the comm module 130 may include a port for connection of a communication cable, for example a CAT5 cable, to enable communication with external equipment. In certain embodiments, the comm module 130 may include a port for a removable media, for example a USB port to connect to a "thumb drive," or a drive configured to read and/or write to a removable media, for example a CD or DVD.

The display 132 may be any audio or visual device as known to those of skill in the art. In certain embodiments, the display 132 may include a color or monochrome two-dimensional visual display that may include one or more of light emitting diodes (LEDs), liquid crystals, "electronic paper" such as electrophoretic display technologies, or electroluminescent elements. In certain embodiments, the display 132 may be an audio device (132b in FIG. 3) such as a speaker, buzzer, or tone generator. In certain embodiments, the display 132 may be a visual indicator (132a in FIG. 3) such as a single monochrome LED, a group of LEDs of various colors, an incandescent bulb, or a linear array of single light-emitting elements.

The alarm 134 may include visual indicators, for example lights that may be selectably illuminated, or audible indicators, for example a speaker, a tone generator, or a buzzer. In certain embodiments, the alarm 134 may be a visual element provided on the display 132. In certain embodiments, a visual or audible signal may be provided continuously or during non-alarm conditions. For example, a tone of a first frequency or combination of frequencies may be provided when the caregiver is operating the resuscitator within the desired range of pressure. In certain embodiments, the visual or audible signal may change, for example to a tone of a second frequency or combination of frequencies, when the pressure exceeds the desired range.

In certain embodiments, the resuscitator 100 may have a disposable portion, for example the bag 110, flow passage 114, and mask 112, to which a re-useable portion, for example the sensor module 120, is attached. In certain embodiments, the disposable portion may include a sensor, for example a flow sensor such as shown in FIG. 6, that functionally connects to the processor 122. In certain embodiments, the entire resuscitator 100 may be disposable.

Figure 5:
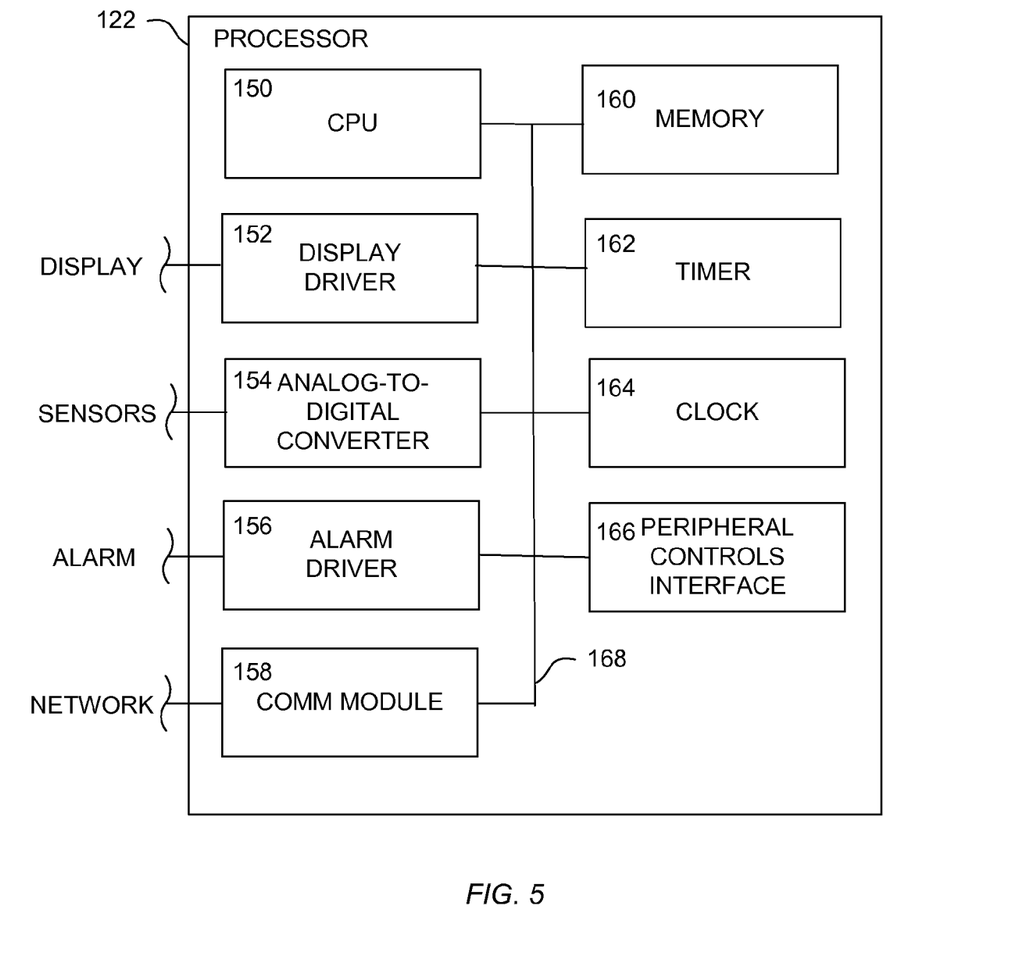
FIG. 5 is a block diagram of the example processor that is part of the sensor module of FIG. 4 according to certain aspects of the present disclosure.

FIG. 5 is a block diagram of the example processor 122 that is part of the sensor module 120 of FIG. 4 according to certain aspects of the present disclosure. The processor 122 may include one or more of a central processor unit (CPU) 150, a display driver 152, an analog-to-digital converter (ADC) 154, an alarm driver 156, a comm module 158, a memory 160, a timer 162, a clock 164, and a peripheral control interface 166 that are interconnected by an internal network 168. Various components may be connected directly to other modules of the sensor module 122, for example the display driver 152 may be connected directly to the display 132. In certain embodiments, various components may be connected to other modules of the sensor module 122 through the internal network 168, comm module 158, and an external network.

The memory 160 may include transitory computer-readable media such as random access memory (RAM) as well as non-transitory computer-readable media that may include magnetically encodable media such as hard disks, solid-state memory (SSD), flash memory data storage devices such as thumb drives, and read-only memory (ROM). The memory 160 may be configured to store operational instructions that may be retrieved by the CPU 150 to configure the CPU 150 so as to be able to perform various functions. The memory 160 may also contain a look-up table comprising limits or other information that may be used to interpret the measurements of the various sensors, alone or in combination. In certain embodiments, the memory may store instructions and information related to the operation and testing of the resuscitator, for example battery life, self-test procedures, errors code, etc. In certain embodiments, the memory 160 may store calibration instructions and information for use in calibrating elements of the resuscitator 100.

The peripheral controls interface 166 may be coupled to external devices within the sensor module 120, for example a touchscreen, buttons, and switches, to allow a user to interact with the CPU 150 so as to initiate desired functions. In certain embodiments, the peripheral controls interface 166 may be operatively coupled to the valve assembly 116 so as, for example, to control a restrictor (not shown in FIG. 3) that maintains a desired minimum pressure within the mask 112.

In certain embodiments, the CPU 150 may be configured to receive measurements made by the pressure sensor 126 through the ADC 154. In certain embodiments, the CPU 150 may store a portion of these measurements in the memory 160. In certain embodiments, the CPU 150 may display a portion of the measurements on the display, for example as a measurement-vs.-time curve that may be overlaid with zones of pressure indicating desirable and/or undesirable ranges of pressure. In certain embodiments, the CPU 150 may receive measurements from one or more chemical sensors 128 and analyze the measurements. In certain embodiments, the CPU 150 may provide indications to the caregiver of certain physical conditions associated with the measurements of the chemical sensors 128, for example a warning that the patient has a certain level of an anesthetizing agent in their blood. In certain embodiments, the CPU 150 may provide other information or warnings to the caregiver related to the measured chemical markers in the exhaled breath as known to those of skill in the art.

In certain embodiments, the CPU 150 may provide real-time guidance to a caregiver using the resuscitator 100 by providing a visual or audible metronome signal through the display 132 or alarm 134 at a target rate of inhalation intervals or cycles. In certain embodiments, the CPU 150 may adjust the metronome signal to an upper or lower value, within an acceptable range of rates of inhalation intervals, based on the rate of inhalation intervals as measured by the pressure sensor 126.

In certain embodiments, the CPU 150 may provide real-time guidance to a caregiver using spoken phrases, for example "current rate is 20 breaths per minute, please slow to 12 breaths per minute," through a display 132 that comprises a speaker. In certain embodiments, the CPU 150 may provide real-time guidance to a caregiver through a display 132 that comprises a flashing, variably colored light, for example a light flashing at a target inhalation interval with a color that indicates whether the resuscitator is currently being actuated at a rate that is higher than, within, or less than an acceptable range. In certain embodiments, the current rate being displayed may be a time-average of a past number, for example three, inhalation intervals.

In certain embodiments, the CPU 150 may combine measurements from multiple sensors to calculate other parameters related to the patient's condition or the resuscitation actions, for example a tidal volume or exhalation pressure.

In certain embodiments, the CPU 150 may store an entire history of a resuscitation event, for example including one or more of pressures, partial pressures, and measured chemical markers, and download this history through the comm modules 158 and 130 to an external system, for example a personal computer (PC). This history may enable a review of the resuscitation event and the actions of the caregiver during the event. In the case where a patient does not survive, this history may provide evidence of factors, such as asthma, that may have contributed to the patient's death.

If the resuscitator 100 were used with a manikin or other training aid, this history may provide the ability to quantitatively evaluate the performance of the user.

In certain embodiments, the CPU 150 may be configured to accept new programming instructions, for example built-in operating system (BIOS) programming and settings, firmware, or software, or new information, for example a look-up table of limits and parameters, and store these instructions and information in memory 160.

Figure 6A:
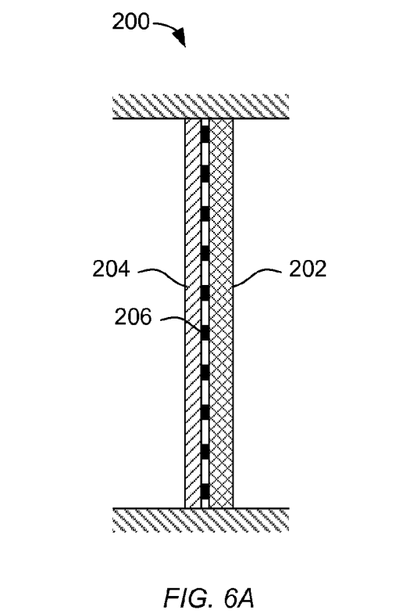
FIGS. 6A-6B are cross-sections of an exemplary flow sensor according to certain aspects of the present disclosure.
Figure 6B:
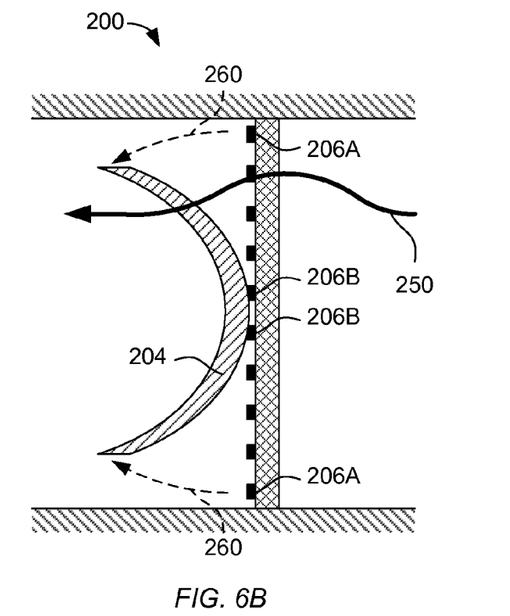

FIGS. 6A-6B are cross-sections of an exemplary flow sensor 200 according to certain aspects of the present disclosure. The flow sensor 200 includes a rigid porous plate 202 having a plurality of contacts 206 distributed over the plate 202. A flexible disk 204 is attached, in certain embodiments, to the middle of plate 202. FIG. 6A depicts the configuration of the sensor 200 in the absence of a flow of gas past the sensor. All, or at least a majority, of the contacts 206 are in contact with or otherwise actuated by the flexible disk 204 so as to provide an indication that the disk is in a first configuration, for example flat against the plate 202.

FIG. 6B depicts the sensor 200 while a gas flows past the sensor 200, as indicated by the flow path 250. The flexible disk 204 deflects as indicated by the arrows 260 to a second configuration wherein only sensors 206B are in contact with disk 204 while sensors 206A are not in contact with the disk 204. The number of contacts 206A vs. 206B provides an indication of the amount of deflection of disk 204 and therefore an indication of the rate of flow of the gas passing the sensor 200.

If a sensor 200 is placed in the flow passage 114 between the mask 112 and the valve assembly 116, or in the exhalation port outside of the valve assembly 116, it may be possible to measure the exhalation flow rate. In certain embodiments, the CPU 150 may combine the measurement from pressure sensor 126 and the measurement from flow sensor 200 to calculate a tidal volume.

Figure 6C:
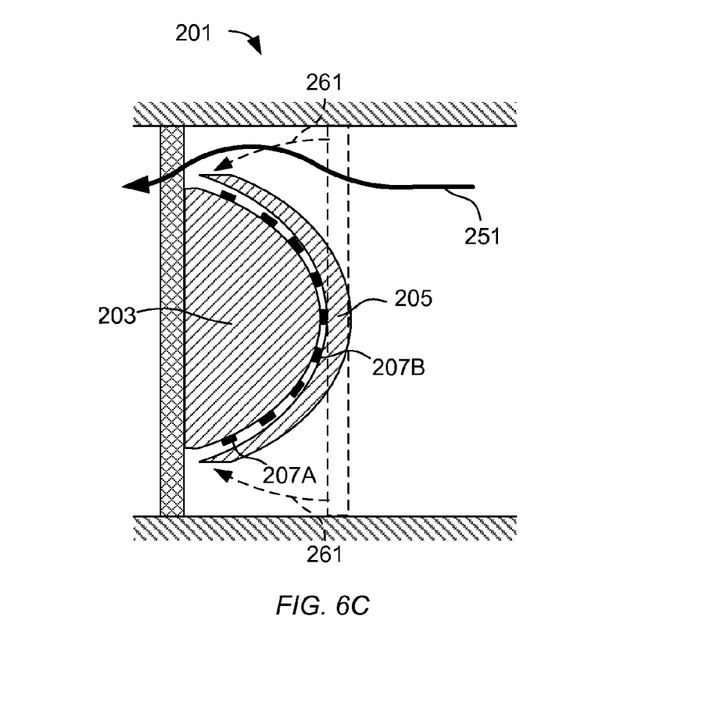
FIG. 6C depicts another embodiment of the flow sensor according to certain aspects of the present disclosure.

FIG. 6C depicts another embodiment 201 of the flow sensor according to certain aspects of the present disclosure. The flow sensor 201 has contacts 207A and 207B that are placed on the surface of a curved structure 203 that is disposed downstream of the flexible disk 205, with respect to the direction of measurement. The disk 205 bends away from the undeformed position, shown in dashed line, as indicated by the arrows 261 in response to the flow 251. As the disk 205 increasingly bends, it comes into contact with an increasing number of the contacts 207B. By comparing the number and position of contacts 207B that are in contact with the disk 205 to the number and location of the contacts 207A that are not in contact with the disk 205, the configuration of the disk 205 can be determined.

Figure 7A:
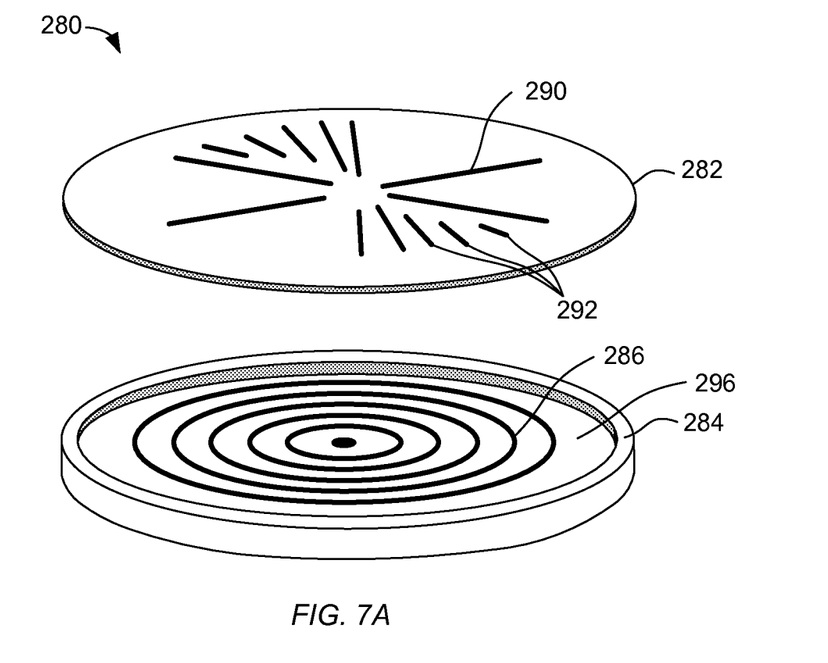
FIG. 7A is an exploded view of an exemplary pressure sensor 280 according to certain aspects of the present disclosure.

FIG. 7A is an exploded view of an exemplary pressure sensor 280 according to certain aspects of the present disclosure. The sensor 280 includes a flexible disk 282 and a wall 284 that, in this embodiment, is circular. In this embodiment, the wall 284 is formed on a substrate 296 with a series of conductive rings 286 formed on the substrate 296 within the wall 284. The disk 282 has, in this embodiment, a series of radial conductive strips 290, 292 formed on the underside (the disk 282 is shown as transparent in FIG. 7A to make the strips 290, 292 visible). In certain embodiments, the strips 292 are of variable length and arranged such that more strips 292 contact the rings 286 as the disk 282 is increasingly deformed.

FIG. 7A is an exploded view of an exemplary pressure sensor 280 according to certain aspects of the present disclosure. The sensor 280 includes a flexible disk 282 and a wall 284 that, in this embodiment, is circular. In this embodiment, the wall 84 is formed on a substrate 296 with a series of conductive rings 286 formed on the substrate 296 within the wall 284. The disk 282 has, in this embodiment, a series of radial conductive strips 290, 292 formed on the underside (the disk 282 is shown as transparent in FIG. 7A to make the strips 290, 292 visible). In certain embodiments, the strips 292 are of variable length and arranged such that more strips 292 contact the rings 286 as the disk 282 is increasingly deformed.

Figure 7B:
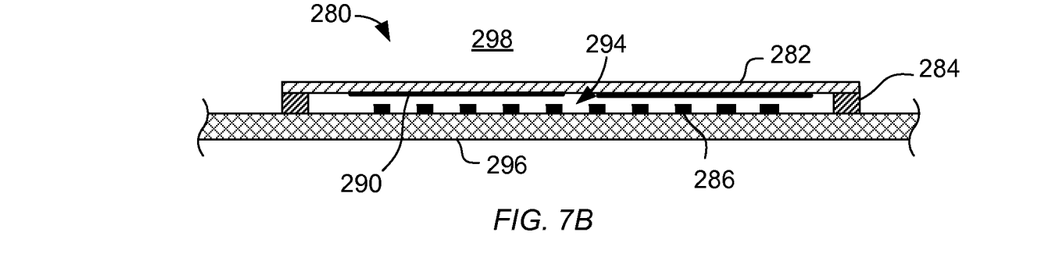
FIGS. 7B-7C are cross-sections of the assembled pressure sensor 280 of FIG. 7A according to certain aspects of the present disclosure.
Figure 7C:
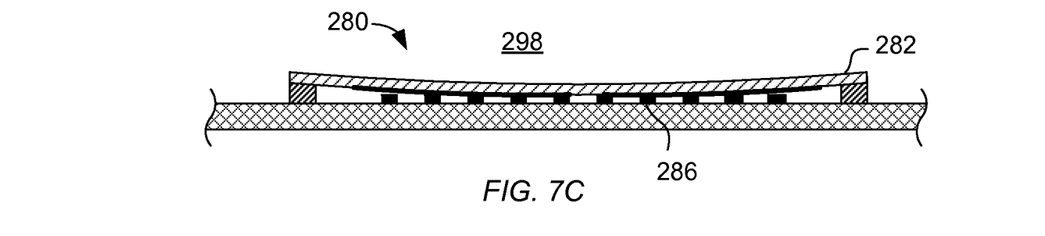

FIGS. 7B-7C are cross-sections of the assembled pressure sensor 280 of FIG. 7A according to certain aspects of the present disclosure. This disk 282 is sealingly attached to the wall 284 so as to form an interior volume 294 over the substrate 296. FIG. 7B shows the pressure sensor 280 in an initial configuration wherein the pressures within interior volume 294 and external volume 298 are equal. In certain embodiments, the external volume 298 may be the interior of flow passage 114 of FIG. 3. In certain embodiments, the interior volume 294 may be vented to the ambient atmosphere, for example external to the flow passage 114, such that pressure measured by the pressure sensor 280 is gauge pressure. As the pressure in the external volume 298 increases, the disk 282 will deform as shown in FIG. 7C and one or more of the radial strips 290, 292 (not visible in FIGS. 7B-7C) on disk 282 will contact one or more of the concentric rings 286. By determining which rings 286 are interconnected by contact with the strips 290, 292, for example by measuring the resistance between pairs of rings 286, using a resistance measurement device (not shown in FIGS. 7A-7C), the deformed shape of the disk 282 can be determined and therefore the pressure in the external volume 298 can be determined. With the appropriate arrangement of the radial strips 292, the change in resistance may be non-linear with increased deformation, thereby at least partially compensating for any non-linear deformation of the disk 282 in response to an incremental change in the pressure in external volume 298. In the example wherein the external volume 298 is the interior of flow passage 114, the pressure in the external volume 298 typically fluctuates between ambient pressure and a higher pressure, thus deflecting the disk 282 against the concentric rings 286 to a greater or lesser degree.

It will be apparent that the disposition of the concentric rings 286 and radial conductive strips 290, 292 may be interchanged such that the concentric conductive rings are formed on the underside of the disk 282 while radial conductive lines of varying length are provided on the surface of substrate 296 within the wall 284 without departing from the scope of this disclosure. Methods of selectably measuring the resistance between pairs of the rings 286, in the embodiment shown in FIGS. 7A-7C, or of radial conductive lines formed on the substrate, in an alternate embodiment, are known to those of skill in the art and are not shown herein.

Figure 8:
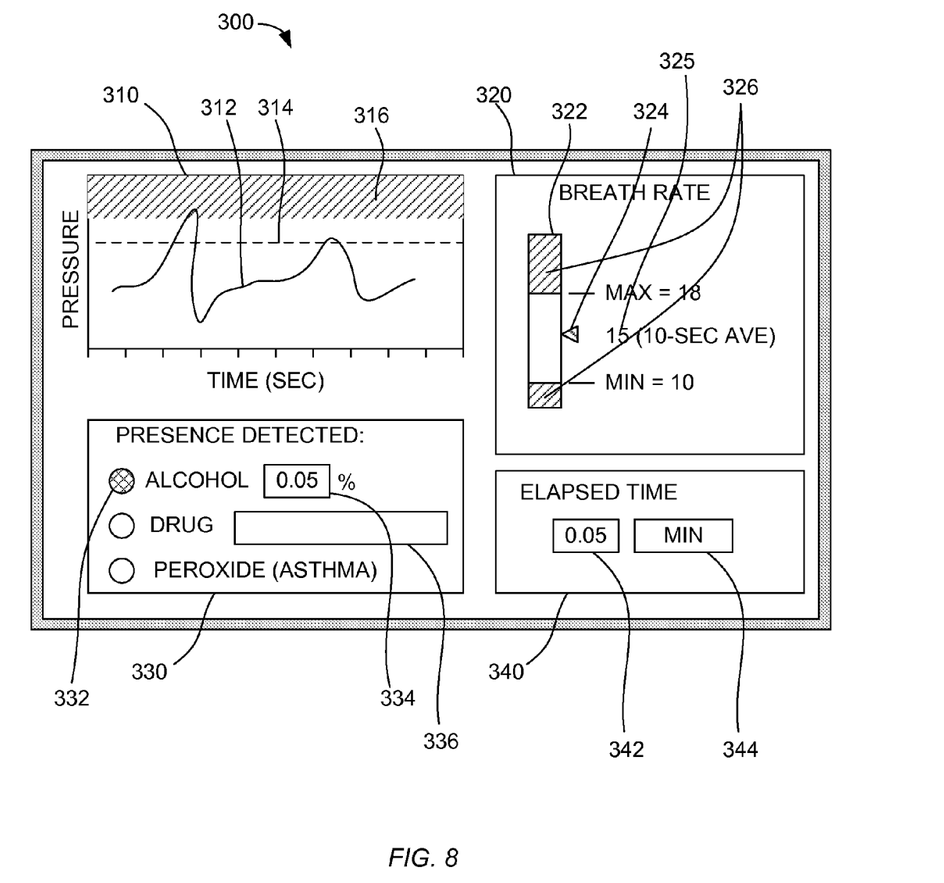
FIG. 8 is an exemplary display of information provided by the processor according to certain aspects of the present disclosure.

FIG. 8 is an exemplary display 300 of information provided by the processor 122 according to certain aspects of the present disclosure. The display 300 depicts examples of four sections 310, 320, 330, and 340 each displaying one or more examples of information. In certain embodiments, the display 300 may provide more or fewer elements of information.

Section 310 displays an exemplary pressure-vs.-time curve 312, with the current time at the right. The plot is overlaid with a target peak inhalation pressure line 314 and an excess-pressure area 316.

Section 320 displays the breath rate, i.e. the rate of inhalation intervals. The display 320 includes a marker 324 indicating the current time-averaged breath rate within a range bar 322 with minimum and maximum rates indicated with labels and shaded areas 326. The value is shown as a numerical value 325 that, in certain embodiments, may include a notation, for example a notation that the value is a 10-second average.

Section 330 displays visual indicators 332 associated with various physical attributes. The box 334 displays the calculated blood-alcohol content based on the measured marker in the patient's breath. The box 336 would identify a drug, if detected.

Section 340 displays the elapsed time since the initiation of a resuscitation event. The box 342 displays the value and box 344 displays the units of time, which may initially be "seconds" and later change to "minutes" after a certain time interval has elapsed.

It can be seen that the disclosed embodiments of a resuscitation devices having an onboard processor provides improved access to accurate measurements of variables related to both the functioning of the resuscitation device as well as the physiological functioning of the patient. These variables may be easily read by the caregiver during the procedure and/or stored for later analysis or training purposes.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

The terms "include," "have," and the like are intended to be inclusive in a manner similar to the term "comprise" as "comprise" is interpreted when employed as a transitional word in a claim.

No claim element is to be construed under the provisions of 35 U.S.C. §112, sixth paragraph, unless the element is expressly recited using the phrase "means for" or, in the case of a method claim, the element is recited using the phrase "step for."

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A resuscitator comprising:
   a patient airway interface device;
   a bag;
   a flow passage coupled between the bag and patient airway interface device; and
   a sensor assembly comprising:
      a display;
      a flow sensor coupled to the flow passage and configured to provide a measurement of at least one flow parameter, the flow sensor comprising:
         a porous plate extending across the flow passage, the porous plate having a plurality of contacts comprising individual sensors, and
         a flexible disk positioned to engage the plurality of contacts, wherein the individual sensors detect contact with the flexible disk, and deformation of the flexible disk due to a fluid flow through the flow passage causes the flexible disk to disengage from at least one of the plurality of contacts; and
      a processor coupled to the display and the flow sensor, the processor configured to receive the measurement from the flow sensor and provide information on the display based on the received measurement.

2. The resuscitator of claim 1, wherein:
   the sensor assembly further comprises a pressure sensor; and
   the information provided on the display further comprises pressure information.

3. The resuscitator of claim 2, wherein the pressure information comprises a pressure-vs-time curve.

4. The resuscitator of claim 2, wherein the information further comprises an alarm.

5. The resuscitator of claim 2, wherein the information further comprises real-time guidance related to operation of the resuscitator.

6. The resuscitator of claim 5, wherein the real-time guidance comprises a metronome signal of a target rate of inhalation intervals.

7. The resuscitator of claim 6, wherein the metronome signal comprises an audible signal.

8. The resuscitator of claim 6, wherein the processor is configured to adjust the metronome signal based on a current measured rate of inhalation intervals.

9. The resuscitator of claim 2, wherein:
the information provided on the display comprises a tidal volume.

10. The resuscitator of claim 9, wherein the flexible disk has a first configuration associated with a zero flow rate and a plurality of second positions respectively associated with a plurality of flow rates.

11. The resuscitator of claim 1, wherein:
the sensor assembly further comprises a chemical sensor; and
the information provided on the display further comprises information on chemical markers associated with certain physical attributes.

12. The resuscitator of claim 11, wherein the information on chemical markers comprises information regarding one or more of a level of alcohol in the patient's blood, a level of a drug in the patient's blood, a peroxide level in an exhaled breath of a patient, or a pH of the exhaled breath.

13. The resuscitator of claim 1, wherein:
the sensor assembly comprises a memory coupled to the processor; and
the processor is configured to store a portion of the measurement of at least one parameter in the memory.

14. The resuscitator of claim 13, wherein the processor is configured to retrieve a portion of the measurement from the memory and provide the retrieved portion of the measurement to an external system.

15. The resuscitator of claim 14, wherein the sensor assembly comprises a communication module coupled to the processor and configured to communicate wirelessly with the external system.

16. The resuscitator of claim 1, wherein the patient airway interface device comprises a mask.

17. The resuscitator of claim 1, wherein the patient airway interface device comprises an endotracheal tube.

18. The resuscitator of claim 1, wherein the sensor assembly further comprises a communication system configured to wirelessly communicate with external equipment.

19. A resuscitator comprising:
a patient airway interface device;
a bag;
a flow passage coupled between the bag and patient airway interface device; and
a sensor assembly comprising:
an indicator;
a flow sensor coupled to the flow passage and configured to provide a measurement of at least one parameter, the at least one a flow sensor comprising:
a porous plate extending across the flow passage, the porous plate having a plurality of actuable sensor contacts, and
a flexible disk positioned to engage and actuate the plurality of sensor contacts, wherein deformation of the flexible disk due to a fluid flow through the flow passage causes the flexible disk to disengage from at least one of the plurality of actuable sensor contacts; and
a processor coupled to the indicator and the flow sensor, the processor configured to receive the measurement from the flow sensor and actuate the indicator based on the received measurement.

20. The resuscitator of claim 19, wherein the indicator is an audio device.

21. The resuscitator of claim 19, wherein the indicator is a visual device.

22. The resuscitator of claim 19, wherein the processor actuates the indicator so as to provide real-time guidance related to operation of the resuscitator.

23. The resuscitator of claim 22, wherein the real-time guidance comprises time-averaged information related to a target rate of inhalation intervals.

24. The resuscitator of claim 19, wherein:
the sensor assembly further comprises a memory coupled to the processor;
the processor is configured to store a portion of the measurement in the memory;
the sensor assembly further comprises a communication module coupled to the processor and configured to communicate wirelessly with an external system; and
the processor is configured to retrieve a portion of the measurement from the memory and provide the retrieved portion of the measurement to the external system.

25. The resuscitator of claim 19, wherein the patient airway interface device comprises a mask.

26. The resuscitator of claim 19, wherein the patient airway interface device comprises an endotracheal tube.

27. The resuscitator of claim 19, wherein the sensor assembly further comprises a communication system configured to wirelessly communicate with external equipment.

28. A method comprising the steps of:
measuring in the exhaled breath of a patient using at least one flow sensor comprising:
a porous plate extending across a flow passage, the porous plate having a plurality of contacts comprising individual sensors, and
a flexible disk positioned to engage the plurality of contacts, wherein the individual sensors detect contact with the flexible disk, and deformation of the flexible disk due to a fluid flow through the flow passage causes the flexible disk to disengage from at least one of the plurality of contacts; and
actuating an indicator so as to provide information related to the flow rate measurement including at least one of a breath rate, a tidal volume, or a condition of the patient.

29. The method of claim 28, further comprising the step of:
actuating an indicator so as to provide guidance related to achieving at least one of a target breath rate and a target tidal volume.

* * * * *

UNITED STATES PATENT AND TRADEMARK OFFICE
CERTIFICATE OF CORRECTION

PATENT NO. : 9,446,211 B2  
APPLICATION NO. : 13/829281  
DATED : September 20, 2016  
INVENTOR(S) : Christopher Varga et al.

Page 1 of 1

It is certified that error appears in the above-identified patent and that said Letters Patent is hereby corrected as shown below:

In the Claims

Column 12, Line 37:

Change "measuring in" to --measuring a flow rate in--

Signed and Sealed this  
Third Day of January, 2017

Michelle K. Lee  
*Director of the United States Patent and Trademark Office*